(12) United States Patent
Yu et al.

(10) Patent No.: US 6,187,642 B1
(45) Date of Patent: Feb. 13, 2001

(54) METHOD AND APPARATUS FOR MAKING MOSFET'S WITH ELEVATED SOURCE/DRAIN EXTENSIONS

(75) Inventors: Bin Yu, Sunnyvale; Judy Xilin An, San Jose, both of CA (US)

(73) Assignee: Advanced Micro Devices Inc., Sunnyvale, CA (US)

(*) Notice: Under 35 U.S.C. 154(b), the term of this patent shall be extended for 0 days.

(21) Appl. No.: 09/334,119

(22) Filed: Jun. 15, 1999

Related U.S. Application Data

(63) Continuation-in-part of application No. 08/986,065, filed on Dec. 5, 1997, which is a continuation-in-part of application No. 08/534,454, filed on Sep. 27, 1995, now Pat. No. 5,849,486, which is a continuation-in-part of application No. 08/304,657, filed on Sep. 9, 1994, now Pat. No. 5,632,957, which is a continuation-in-part of application No. 08/271,882, filed on Jul. 7, 1994, which is a continuation-in-part of application No. 08/146,504, filed on Nov. 1, 1993, now Pat. No. 5,605,662, which is a continuation-in-part of application No. 08/859,044, filed on May 20, 1997, which is a continuation-in-part of application No. 08/708,262, filed on Sep. 6, 1996.

(51) Int. Cl.$^7$ .................... H01L 21/336; H01L 21/3205; H01L 21/331; H01L 21/44; H01L 21/22
(52) U.S. Cl. .................... 438/300; 438/301; 438/356; 438/592; 438/563; 438/663
(58) Field of Search .................... 438/301, 356, 438/300, 303–307, 592, 595–596, 563, 663–664

(56) References Cited

U.S. PATENT DOCUMENTS

| | | | |
|---|---|---|---|
| 5,200,352 | * | 4/1993 | Pfiester .................... 437/44 |
| 5,319,232 | * | 6/1994 | Pfiester .................... 257/344 |
| 5,496,750 | * | 3/1996 | Moslehi .................... 437/41 |
| 5,504,031 | * | 4/1996 | Hsu et al. .................... 437/57 |
| 5,539,229 | * | 7/1996 | Noble, Jr. et al. .................... 257/301 |
| 5,600,165 | * | 2/1997 | Tsukamoto et al. .................... 257/323 |
| 5,693,974 | * | 12/1997 | Hsu et al. .................... 257/369 |

OTHER PUBLICATIONS

Wong S.S., D.R. Bradbury, D.C. Chen & K.Y. Chiu: "Elevated Source/Drain MOSFET": IDEM 1984, pp. 634–635.

Mark Rodder and D. Yeakley: "Raised Source/Drain MOSFET with Dual Sidewall Spacers": IEEE Electron Device Letters, vol. 12, Mar. 1991, pp. 89–91.

C.–P. Chao, K.E. Violette, S. Unnikrishnan, M. Nandakumar, R.L. Wise, J.A. Kittl, Q.–Z. Hong, and I.–C. Chen: "Low Resistance Ti or Co Salicided Raised Source/Drain Transistors for Sub–0.13 μm CMOS Technologies": IEDM Technology Digest, Dec. 1997.

* cited by examiner

Primary Examiner—Donald L. Monin, Jr.
Assistant Examiner—S. H. Rao
(74) Attorney, Agent, or Firm—LaRiviere, Grubman & Payne, LLP

(57) ABSTRACT

The inventive method provides improved semiconductor devices, such as MOSFET's with raised source/drain extensions on a substrate with isolation trenches etched into the surface of the substrate. The inventive method provides thin first dielectric spacers on the side of a gate and gate oxide and extend from the top of the gate to the surface of the substrate. Raised source/drain extensions are placed on the surface of a substrate, which extend from the first dielectric spacers to the isolation trenches. Thicker second dielectric spacers are placed adjacent to the first dielectric spacers and extend from the top of the first dielectric spacers to the raised source/drain extensions. Raised source/drain regions are placed on the raised source/drain extensions, and extend from the isolation trenches to the second dielectric spacers. The inventive semiconductor devices provide for very shallow source drain extensions which results in a reduced short channel effect.

5 Claims, 5 Drawing Sheets

METHOD AND APPARATUS FOR MAKING MOSFET'S WITH ELEVATED SOURCE/DRAIN EXTENSIONS

This Appln is a CIP of Ser. No. 08/986,065, filed Dec. 5, 1997, which is a CIP of Ser. No. 08/534,454, filed Sep. 27, 1995, now U.S. Pat. No. 5,849,486, which is CIP of Ser. No. 08/304,657, filed Sep. 9, 1994, now U.S. Pat. No. 5,632,957, which is CIP of Ser. No. 08/271,882, filed Jul. 7, 1994, which is CIP of Ser. No. 08/146,504, filed Nov. 1, 1993, now U.S. Pat. No. 5,605,662, which is CIP of Ser. No. 08/859,044, filed May 20, 1997, which is CIP of Ser. No. 08/708,262, filed Sep. 9, 1996.

FIELD OF THE INVENTION

The present invention relates to MOSFET devices. Even more particularly, the present invention relates to MOSFET devices with raised (or elevated) source/drain extensions.

BACKGROUND OF THE INVENTION

In the prior art, MOSFETS with raised source/drain regions use source/drain extensions to connect a channel with the raised source/drain regions. FIG. 1 is a schematic view of a prior art MOSFET 10 with raised source/drain regions 11. The raised source/drain regions 11 are built on top of a substrate 12 surface. A gate oxide 14 is placed on the surface of the substrate 12 between the raised source/drain regions 11. A gate 15 is placed over the gate oxide 14. Side spacers 16 are placed adjacent to the gate 15 and gate oxide 14 and on the substrate 12, separating the gate 15 and gate oxide 14 from the source/drain regions 11. Source/drain extensions 17 are formed at and below the surface of the substrate 12 extending under the source/drain regions 11, the side spacers 16, and partly under the gate oxide 14 and the gate 15. Isolation trenches 19 are cut into the surface of the substrate 12 around the source/drain extensions 17 to isolate the MOSFET 10. The source/drain extensions 17 may be created through various processes with various doping concentrations. Throughout the specification and claims the phrase "source/drain extensions" will also include source/drain extension type structures created through various means such as lightly-doped-drain implants.

Deep source/drain junctions increase short-channel effects. An increased short-channel effect causes an increased off stage leakage current.

Elevated or raised source/drain MOS transistors have been developed to achieve shallow junctions while maintaining low sheet resistivity in the source/drain regions, as well as low silicided contact resistance without significantly increasing the junction leakage. Such raised source/drains are discussed in "Elevated Source/Drain MOSFET", by S. S. Wong, et al. in IEDM Tech. Digest, December 1984, p. 634, and in "Raised Source/Drain MOSFET With Dual Sidewall Spacers" by Mark Rodder and D. Yeakley, IEEE Electron Device Letters, Vol. 12(3), March 1991, p. 89, and in "Low Resistance Ti or Co Salicided Raised Source/Drain Transistors For Sub-0.13 µm CMOS Technologies" by C. P. Chao, et al., IEDM Tech. Digest., December 1997. Source/drain junctions have been elevated, however, only in the heavily doped regions. In other words, the junction depths of source/drain extensions have not been reduced.

BRIEF SUMMARY OF THE INVENTION

It is an object of the invention to provide method and apparatus for reducing short channel effects.

It is another object of the invention to provide a MOSFET with shallower source/drain extensions.

It is another object of the invention to provide raised source/drain extensions.

Accordingly, the foregoing objects are accomplished by creating a MOSFET with partially raised source/drain extensions.

Other features of the present invention are disclosed or apparent in the section entitled: "DETAILED DESCRIPTION OF THE INVENTION."

BRIEF DESCRIPTION OF DRAWINGS

For a fuller understanding of the present invention, reference is made to the accompanying drawings wherein.

Figure 1:
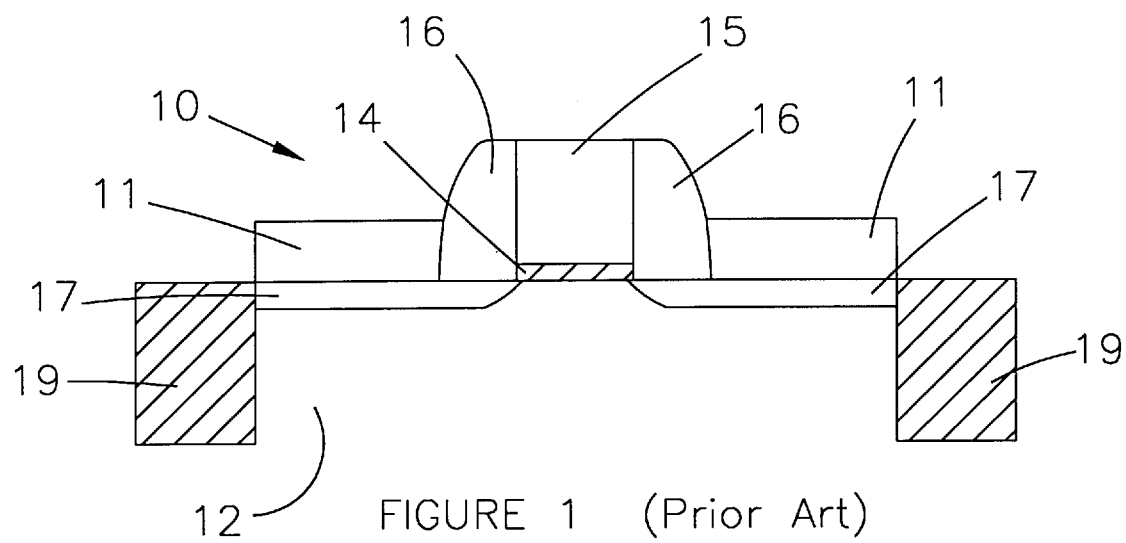
FIG. 1 is a schematic view of a MOSFET used in the prior art.

Reference numbers refer to the same or equivalent parts of the present invention throughout the several figures of the drawing.

DETAILED DESCRIPTION OF THE INVENTION AND BEST MODE OF THE INVENTION

Figure 2:
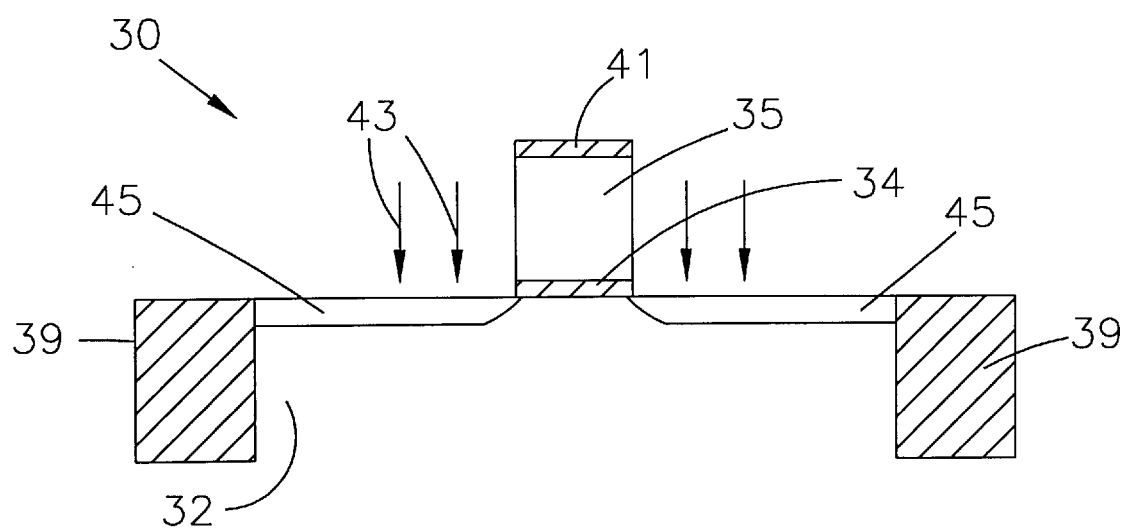
FIG. 2 is a schematic view of a substrate with the first phase of a MOSFET being formed according to an embodiment of the invention.

FIG. 2 is a schematic view of part of a substrate 32 and the first phase of a MOSFET 30 being formed on the substrate 32. Isolation trenches 39 are etched into the surface of the substrate 32. The first phase of the MOSFET 30 has a gate 35 placed on a gate oxide 34 placed on the surface of the substrate 32. An anti-reflective coating (ARC) 41 is placed on the gate 35. In the preferred embodiment, the anti-reflective coating is silicon oxynitride (SiON) with a thickness of 200–300 Å (angstroms). A low-KeV (e.g. 1–10 KeV) dopant implantation 43 is used to create very shallow implant junctions 45. In this example of a preferred embodiment, an N-type implant is used.

Figure 3:
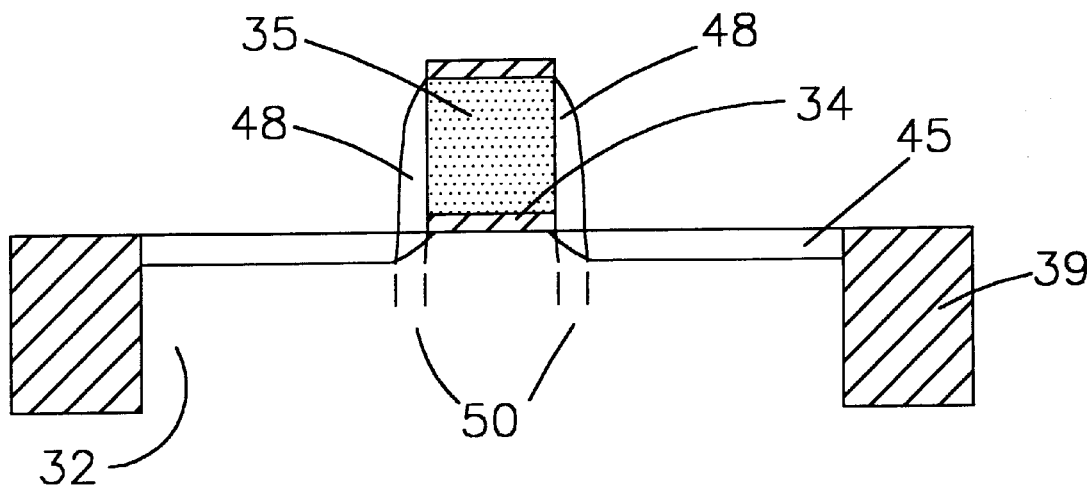
FIG. 3 is a schematic view of the MOSFET in FIG. 2 with first dielectric spacers.

In this example of the preferred embodiment, a deposit-and-etch-back process using a low temperature chemical vapor deposition at less than 400° C. is used to form first dielectric spacers 48, which are preferably silicon oxide or silicon nitride, as shown in FIG. 3. The first dielectric spacers 48 each have a width 50 of between 150–250 Å

(which is defined as the thickest part of the width of the first dielectric spacers 48). The first dielectric spacers 48 are adjacent to the sides of the gate 35 and gate oxide 34 and extend from the top of the gate 35 to the surface of the substrate 32.

Figure 4:
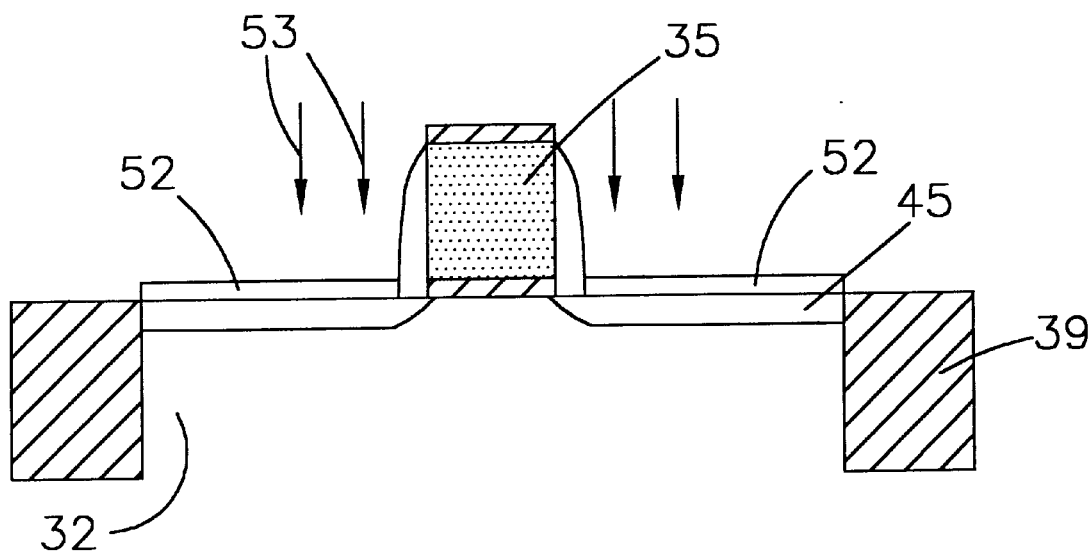
FIG. 4 is a schematic view of the MOSFET in FIG. 3 with a first semiconductor layer.
Figure 5:
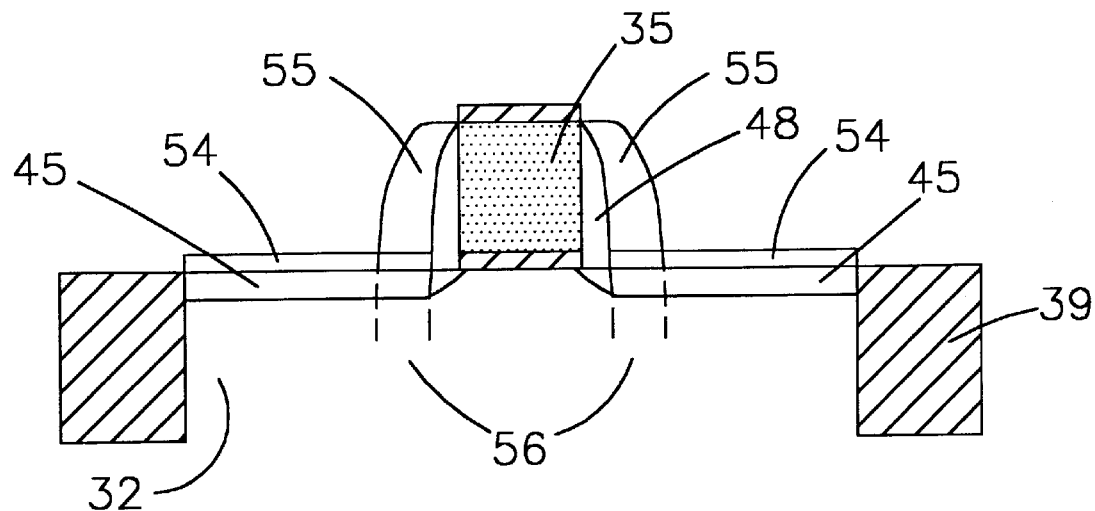
FIG. 5 is a schematic view of the MOSFET in FIG. 4 with second dielectric side spacers.

The surface of the substrate 32 is then subjected to a precleaning. A selective Si (silicon) epitaxial growth at a temperature of 750–900° C. is used to grow first semiconductor layers 52 of a thickness of 200–300 Å, as shown in FIG. 4. A low-Kev (e.g. 1–3 KeV) dopant implantation 53 is used to transform the first semiconductor layers 52 into raised source/drain extensions 54 with a bottom surface adjacent to the implant junctions 45 and a top surface opposite from the bottom surface, as shown in FIG. 5. In this example an N-type implant is used. A deposit-and-etch-back process using a low temperature chemical vapor deposition at less than 400° C. is used to form second dielectric spacers 55, which are preferably silicon oxide or silicon nitride. The second dielectric spacers 55 each have a width 56 of between 300–800 Å (which is defined as the thickest part of the width of the second dielectric spacers 55). The second dielectric spacers 55 are adjacent to the first dielectric spacers 48 and are separated from the gate 35 by the first dielectric spacers 48. The second dielectric spacers 55 extend from the top of the first dielectric spacers 48 to the top surface of the raised source/drain extensions 54.

Figure 6:
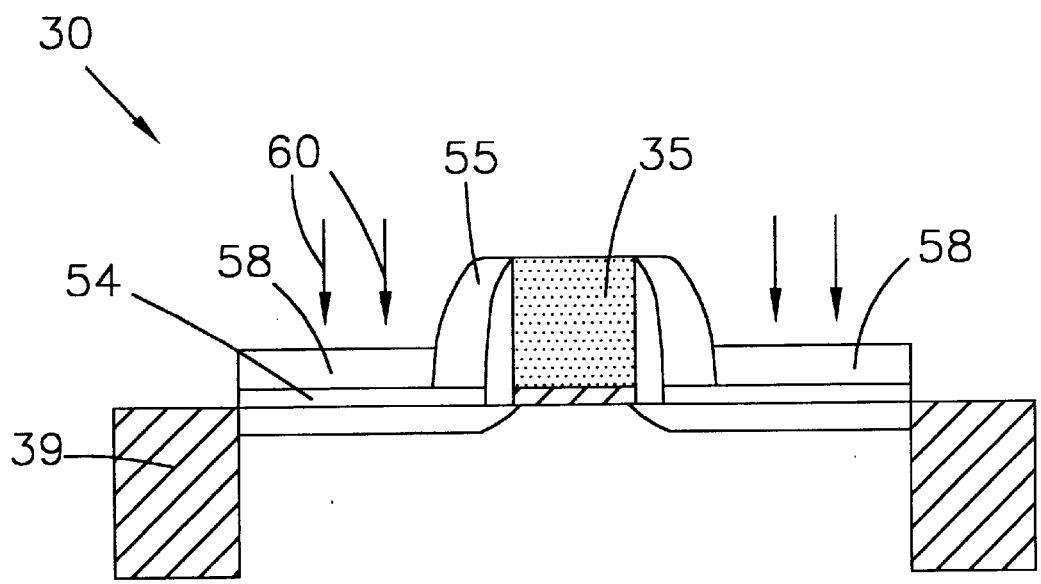
FIG. 6 is a schematic view of the MOSFET in FIG. 5 with a second semiconductor layer.

The top surface of the raised source/drain extensions 54 is subjected to a surface preclean. Then a selective Si epitaxial growth at a temperature of 750–900° C. is used to grow second semiconductor layers 58 of a thickness of 200–300 Å on the top surface of the raised source drain extensions 54 and extending from the isolation trenches to the second dielectric spacers 55, as shown in FIG. 6. The anti-reflective coating 41 is stripped. A higher KeV (e.g. 10–30 KeV) dopant implantation 60 is used to dope the second semiconductor layers 58, and the gate 35. In this example of a preferred embodiment, an N-type implant is used. A rapid-thermal-anneal (RTA) is used to transform the doped second semiconductor layers 58 into raised source/drain regions.

Conventional MOSFET processing is done to form the MOSFET structure 30 into a completed MOSFET, including the silicidation of the raised source/drain junctions. The resulting MOSFET has partially raised source/drain extensions, providing ultra-shallow source/drain junctions, which reduces the short channel effect. If the implant junctions are part of source/drain extensions the implant junctions may be doped at lower doping levels than in conventional source/drain extensions.

Figure 7:
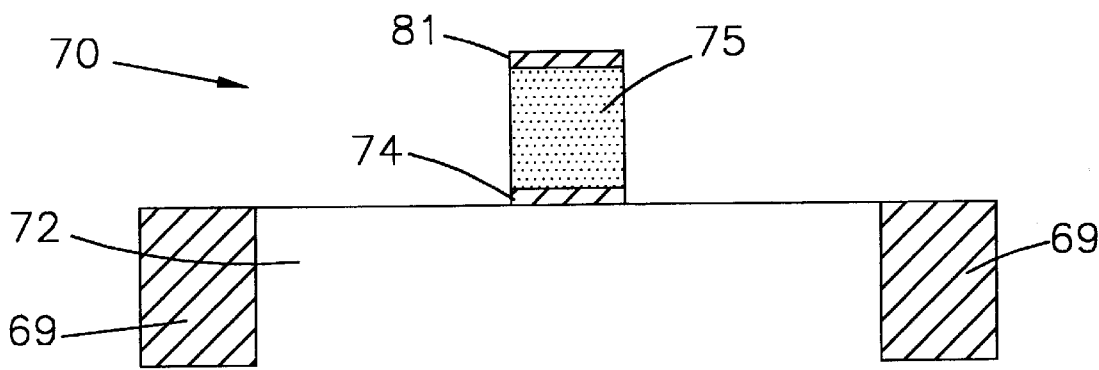
FIG. 7 is a schematic view of a substrate with the first phase of a MOSFET being formed according to another embodiment of the invention.

In another embodiment of the invention, isolation trenches 69 are etched into the surface of the substrate 72 upon which a first phase of a MOSFET 70 is built, as schematically illustrated in FIG. 7. The first phase of the MOSFET 70 has a gate 75 placed on a gate oxide 74 placed on the surface of the substrate 72. An anti-reflective coating (ARC) 81 is placed on the gate 75. In the preferred embodiment, the anti-reflective coating is silicon oxynitride (SiON) with a thickness of 200–300 Å (angstroms).

Figure 8:
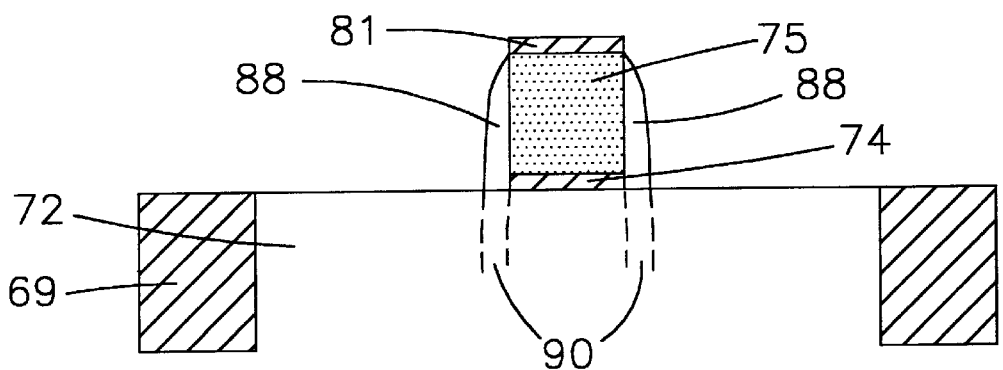
FIG. 8 is a schematic view of the MOSFET in FIG. 7 with first dielectric spacers.

In this example of the preferred embodiment, a deposit-and-etch-back process using a low temperature chemical vapor deposition at less than 400° C. is used to form first dielectric spacers 88, which are preferably silicon oxide or silicon nitride, as shown in FIG. 8. The first dielectric spacers 88 each have a width 90 of between 150–200 Å. The first dielectric spacers 88 are adjacent to the sides of the gate 75 and gate oxide 74 and extend from the top of the gate 75 to the surface of the substrate 72.

Figure 9:
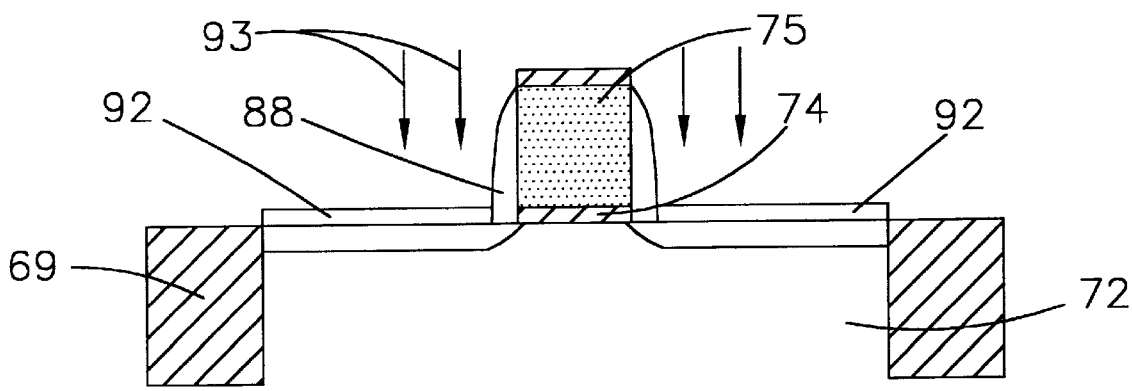
FIG. 9 is a schematic view of the MOSFET in FIG. 8 with a first semiconductor layer.
Figure 10:
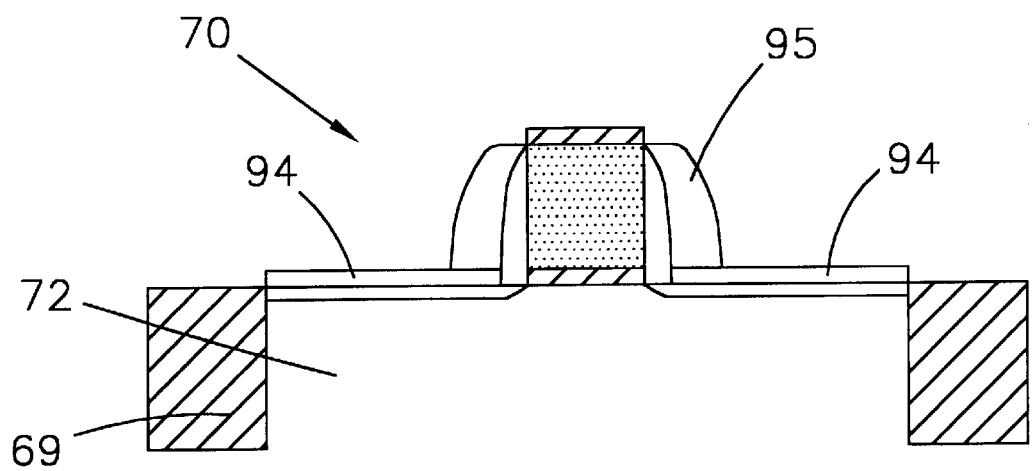
FIG. 10 is a schematic view of the MOSFET in FIG. 9 with second dielectric side spacers.

The surface of the substrate 72 is then subjected to a precleaning. A selective Si (silicon) epitaxial growth at a temperature of 750–900° C. is used to grow first semiconductor layers 92 of a thickness of 200–300 Å, as shown in FIG. 9. A low-Kev dopant implantation 93 is used to transform the first semiconductor layers 92 into raised source/drain extensions 94 with a bottom surface adjacent to the surface of the substrate 72 and a top surface opposite from the bottom surface, as shown in FIG. 10. In this example an P-type implant, such as Boron with an implant energy of 0.5–3 KeV, is used. A deposit-and-etch-back process using a low temperature chemical vapor deposition at less than 400° C. is used to form second dielectric spacers 95, which are preferably silicon oxide or silicon nitride. The second dielectric spacers 95 each have a width 96 of between 300–800 Å. The second dielectric spacers 95 are adjacent to the first dielectric spacers 88 and are separated from the gate 75 by the first dielectric spacers 88. The second dielectric spacers 95 extend from the top of the first dielectric spacers 88 to the top surface of the raised source/drain extensions 94.

Figure 11:
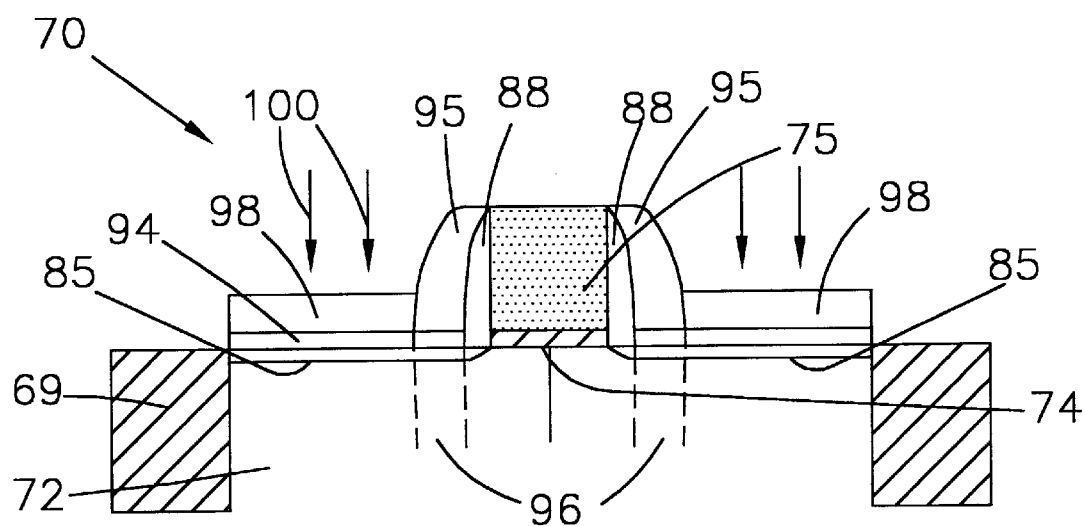
FIG. 11 is a schematic view of the MOSFET in FIG. 10 with a second semiconductor layer.

The top surface of the raised source/drain extensions 94 is subjected to a surface preclean. Then a selective Si epitaxial growth at a temperature of 750–900° C. is used to grow second semiconductor layers 98 of a thickness of 200–300 Å on the top surface of the raised source drain extensions 94 and extending from the isolation trenches to the second dielectric spacers 95, as shown in FIG. 11. The anti-reflective coating 81 is stripped. A dopant implantation 100 is used to dope the second semiconductor layers 98, and the gate 75. In this example of a preferred embodiment, an P-type implant, such as $BF_2$ (Boron difluoride) with an implant energy of 10–30 KeV, is used. A rapid-thermal-anneal (RTA) is used to transform the doped second semiconductor layers 98 into source/drain regions and to complete the transformation of the doped first semiconductor layers 92 into the raised source/drain extensions 94. The rapid-thermal-annealing also causes some of the P-type implant dopant from the first semiconductor layers 92 to migrate to the surface of the substrate 72 forming on and in the surface of the substrate 72 ultra shallow implant junctions 85, which extend from the isolation trenches 69 under the first dielectric spacers 88 to the gate oxide 74.

Conventional MOSFET processing is done to form the MOSFET structure 70 into a completed MOSFET, including the silicidation of the raised source/drain junctions. The resulting MOSFET has fully raised source/drain extensions with minimal source/drain junction depths in the substrate and optimal overlap distance under the gate 75, which reduces the short channel effect.

Information as herein shown and described in detail is fully capable of attaining the above-described object of the invention, it is understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims.

Moreover, it is not necessary for a device or method to address each and every problem sought to be solved by the present invention, for it to be encompassed by the present claims. Furthermore. no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for".

We claim:

1. A method of producing a semiconductor device on a surface of a substrate, comprising the steps of:

forming a gate oxide on the surface of the substrate, where the gate oxide has a first side adjacent to the surface of the substrate and a second side opposite from the first side;

forming a gate on the gate oxide, wherein the gate has a first side adjacent to the second side of the gate oxide and a second side opposite from the first side at a top of the gate;

forming an anti-reflective coat on the gate;

forming first dielectric spacers on the sides of the gate, where the first dielectric spacers have a first side which is adjacent to the gate, a second side opposite to the first side and a width between 150–200 Å;

forming a first semiconductor layer on the surface of the substrate, where the first semiconductor layer extends to the first dielectric spacer, and wherein the first dielectric spacer is between the first semiconductor layer and the gate, and wherein the first semiconductor layer has a first side adjacent to the surface of the substrate and a second side opposite from the first side;

implanting a dopant into the first semiconductor layer;

forming a second dielectric spacer on the second side of the first semiconductor layer and adjacent to the second side of the first dielectric spacer;

forming a second semiconductor layer on the second side of the first semiconductor layer and extending to the second dielectric spacer;

stripping the anti-reflective coat from the gate after forming the second semiconductor layer;

implanting a dopant into the second semiconductor layer; and, annealing the first semiconductor layer and the second semiconductor layer.

2. The method, as recited in claim 1, further comprising the step of implanting a dopant into the surface of the substrate prior to forming the first dielectric spacer, and wherein the dopant is implanted by a dopant beam energy of 1–10 Kev.

3. The method, as recited in claim 2, further comprising the step of etching an isolation trench into the substrate surface.

4. The method, as recited in claim 3, wherein the first dielectric spacers extend from the top of the gate to the surface of the substrate.

5. The method, as recited in claim 4, wherein the second dielectric spacers extend from the top of the first dielectric spacers to the second side of the first semiconductor layer.

* * * * *

UNITED STATES PATENT AND TRADEMARK OFFICE
CERTIFICATE OF CORRECTION

PATENT NO.   : 6,187,642 B1
DATED        : February 13, 2001
INVENTOR(S)  : Bin Yu, Judy Xilin An It is certified that error appears in the above-identified patent and that said Letters Patent is hereby corrected as shown below:

Title page, item 54,
Title,
Delete [MOSFET'S] and replace with -- MOSFETS --.

Item [63],
Delete all listed references regarding Related U.S. Application Data. The references were entered in error at issuance.

Signed and Sealed this

Twenty-fifth Day of September, 2001

Attest:

NICHOLAS P. GODICI
*Attesting Officer*   *Acting Director of the United States Patent and Trademark Office*